United States Patent
Boulens et al.

(10) Patent No.: US 9,308,528 B2
(45) Date of Patent: Apr. 12, 2016

(54) NICKEL-BASED COMPLEXES AND THEIR USE IN A PROCESS FOR THE TRANSFORMATION OF OLEFINS

(71) Applicants: IFP Energies Nouvelles, Rueil-Malmaison (FR); UNIVERSITEIT VAN AMSTERDAM, Amsterdam (NL)

(72) Inventors: Pierre Boulens, Lyons (FR); Pierre-Alain Breuil, Lyons (FR); Joost Reek, BK Amersfoort (NL); Helene Olivier-Bourbigou, Saint Genis-Laval (FR)

(73) Assignees: UNIVERSITEIT VAN AMSTERDAM, Amsterdam (NL); IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/694,216

(22) Filed: Apr. 23, 2015

(65) Prior Publication Data
US 2015/0306589 A1  Oct. 29, 2015

(30) Foreign Application Priority Data
Apr. 28, 2014  (FR) .................... 14 53817

(51) Int. Cl.
| | | |
|---|---|---|
| C07F 15/04 | (2006.01) |
| B01J 31/22 | (2006.01) |
| C07C 2/34 | (2006.01) |
| B01J 31/18 | (2006.01) |
| B01J 31/24 | (2006.01) |

(52) U.S. Cl.
CPC ............ *B01J 31/2295* (2013.01); *B01J 31/188* (2013.01); *B01J 31/24* (2013.01); *C07C 2/34* (2013.01); *C07F 15/04* (2013.01); *B01J 2231/20* (2013.01); *B01J 2531/847* (2013.01); *B01J 2540/30* (2013.01); *C07C 2531/22* (2013.01)

(58) Field of Classification Search
CPC .......... B01J 31/2295; C07F 15/04; C07C 2/34
USPC ..................... 556/13, 20; 585/523
See application file for complete search history.

(56) References Cited

U.S. PATENT DOCUMENTS

| | | | |
|---|---|---|---|
| 6,060,569 A | 5/2000 | Bennett et al. |
| 6,232,483 B1 | 5/2001 | Bennett et al. |
| 8,283,276 B2 | 10/2012 | Reek et al. |
| 2011/0003959 A1 | 1/2011 | Reek et al. |

FOREIGN PATENT DOCUMENTS

EP          2062906 A1    5/2009

OTHER PUBLICATIONS

Search Report and Opinion from corresponding French Patent Application No. 14/53817 dated Jan. 15, 2015.
Patureau, Frederic W. et al. "Supramolecular Hydrogen-Bonding Tautomeric Sulfonamido-Phosphinamides: A Perfect P-Chirogenic Memory" Eur. J. Inorg. Chem. [2012], pp. 496-503.
Terrade, Frederic G. et al. "Synthesis, Coordination Chemistry, and Cooperative Activation of H2 with Ruthenium Complexes of Proton-Responsive METAMORPhos Ligands" Eur. J. Inorg. Chem. [2014], pp. 1826-1835.
Flapper, Jitte et al. "Nickel and Palladium Complexes of Pyridine-Phosphine Ligands as Ethene Oligomerization Catalysts" Organometallics, [2009], vol. 28, pp. 1180-1192.

*Primary Examiner* — Porfirio Nazario Gonzalez
(74) *Attorney, Agent, or Firm* — Millen White Zelano and Branigan, PC; John Sopp; Anthony Zelano

(57) ABSTRACT

The invention describes a novel type of nickel-based complex and its preparation method. The invention also concerns the use of said complex in a process for the transformation of olefins.

20 Claims, No Drawings

NICKEL-BASED COMPLEXES AND THEIR USE IN A PROCESS FOR THE TRANSFORMATION OF OLEFINS

The present invention relates to a novel family of nickel-based complexes and their preparation method. The invention also relates to the use of said complexes as catalysts for chemical transformation reactions.

PRIOR ART

The preparation of complexes based on transition metals for application thereof in various fields of chemistry is known, in particular in the field of catalytic transformations such as hydroformylation, hydrogenation, cross-coupling, olefin oligomerization, etc.

The preparation of complexes of this type depends on the choice of metal and on appropriate ligands. Among these ligands, bidentate ligands represent an important class of ligands used in the preparation of catalysts based on transition metals for various types of catalytic chemical transformations.

The document EP 2 220 099 B1 describes a system of coordination complexes comprising multidentate ligands with formula: $R_1$—$SO_2$—NH—$P(XR_2)_2$; or $R_1$—$SO_2$—N=$PH(XR_2)_2$, or $R_1$—SO(OH)=$NP(XR_2)_2$, in which X is independently O, S, NH, or a bond; in which $R_1$ and $R_2$ are independently selected from an alkyl group, which may or may not be substituted, and an aryl group, in which at least one equivalent of ligand is complexed with one equivalent of a metal selected from rhodium, iridium, the platinum, palladium and the lanthanides. EP 2 220 099 B1 indicates that the coordination complex system may be used as a catalyst for hydroformylation, hydrogenation, polymerisation, isomerisation etc.

In its research, the Applicant has developed a novel family of nickel-based complexes and their preparation method. Surprisingly, it has been shown that such complexes have interesting catalytic properties. In particular, these catalysts have a good activity in the oligomerization of olefins, more precisely in the dimerization of ethylene to form 1-butene. These complexes also have a good selectivity in the dimerization of ethylene to 1-butene.

One aim of the invention is to provide a novel family of nickel-based complexes. In another aspect, a novel catalytic system is proposed comprising said complexes for chemical transformation reactions, in particular for the oligomerization of olefins.

DETAILED DESCRIPTION OF THE INVENTION

Nickel Complexes

The complex of the invention is a nickel-based complex having formula (I)

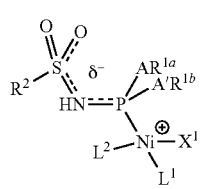

(I)

in which
the atoms P, N, S, O constitute a ligand fragment,
A and A', which may be identical or different, are independently O, S, $NR^3$, or a single bond between the phosphorus atom and a carbon atom,
the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements,
the groups $R^1$, represented in the formula by $R^{1a}$ and $R^{1b}$, with $R^{1a}$ and $R^{1b}$ being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group $R^2$ is selected from alkyl groups which may or may not be cyclic, which may or may not be substituted and which may or may not contain heteroelements, and aromatic groups which may or may not be substituted and which may or may not contain heteroelements,
$L^1$ and $L^2$, which may be identical or different, represent a Lewis base,
$X^1$ is a carbon atom bonded to or forming part of at least one alkyl group, which may or may not be cyclic, which may or may not be unsaturated, which may or may not be substituted and which may or may not contain heteroelements, and an aromatic group which may or may not be substituted and which may or may not contain heteroelements,
$L^1$, $L^2$ and $X^1$ are such that the oxidation number of the nickel is respected, and $\delta^-$ represents the delocalisation of the negative charge over the ligand fragment constituted by the atoms P, N, S and O.

In the context of the present invention, the term "alkyl" is intended to mean a linear or branched hydrocarbon chain containing 1 to 15 carbon atoms, preferably 1 to 10. Preferred alkyl groups are advantageously selected from methyl, ethyl, propyl, isopropyl, butyl, isobutyl and tert-butyl groups. These alkyl groups may be substituted with heteroelements or groups containing heteroelements, such as a halogen or an alkoxy group. The term "alkoxy" substituent means an alkyl-O— group in which the term "alkyl" has the meaning given above. preferred examples of alkoxy substituents are methoxy or ethoxy groups.

The term "cyclic alkyl" means a monocyclic hydrocarbon group containing more than 3 carbon atoms, preferably 4 to 24, more preferably 6 to 12, preferably a cyclopentyl, cyclohexyl, cyclooctyl or cyclododecyl group, or a polycyclic (bi- or tricyclic) group containing more than 3 carbon atoms, preferably 4 to 18, such as adamantyl or norbornyl groups, for example.

The term "linear unsaturated alkyl" or "cyclic unsaturated alkyl" means a linear or cyclic alkyl group containing at least one unsaturated bond, the term "alkyl" and "cyclic alkyl" having the meaning given above.

The term "aromatic" means a mono- or polycylic aromatic group, preferably mono- or bicyclic, containing 5 to 20 carbon atoms. When the group is polycyclic, i.e. it comprises more than one cyclic ring, the cyclic rings may advantageously be condensed in pairs or connected in pairs via a bonds. The aromatic group in accordance with the invention may contain a heteroelement such as nitrogen, oxygen or sulphur.

The term "ligand" as used in the present invention is used indiscriminately to mean one or more of the limiting forms of the ligand with formula 1a), 1b) and/or 1c):

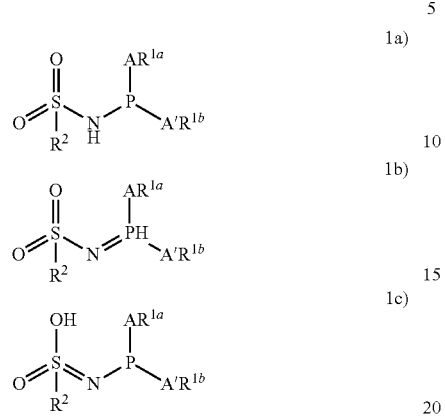

in which
A and A', which may be identical or different, are independently O, S, $NR^3$ or a single bond between the phosphorus atom and a carbon atom, the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements, the groups $R^1$, represented in the formula by $R^{1a}$ and $R^{1b}$, with $R^{1a}$ and $R^{1b}$ being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements, the group $R^2$ is selected from alkyl groups which may or may not be cyclic, which may or may not be substituted and which may or may not contain heteroelements, and aromatic groups which may or may not be substituted and which may or may not contain heteroelements.

The two groups $R^1$ ($R^{1a}$ and $R^{1b}$) may be mutually identical or different. These two groups $R^{1a}$ and $R^{1b}$ may also be bonded together. In such a case, the two groups $R^1$ may correspond to groups such as bis-phenyl or bis-naphthyl.

The ligands of the invention may be prepared by a condensation reaction of a sulphonamide, for example para-n-butylphenyl sulphonamide, and a phosphine halide such as $Ph_2PCl$, in the presence of a Brönsted base such as triethylamine, for example, in a solvent. In solution, these ligands may (co)exist in the three forms 1a), 1b) or 1c) described above.

$L^1$ and $L^2$, which may be identical or different and which may or may not be bonded together, represent a Lewis base. In the context of the present invention, the term "Lewis base" means any chemical entity a constituent of which has one or more free or non-bonding electron pairs. The Lewis bases of the invention in particular correspond to any ligand comprising an oxygen, nitrogen or phosphorus atom with a free or non-bonding electron pair or a π double bond which is capable of forming an $\eta^2$ type coordination with the nickel.

The group $L^2$ of the complex with formula (I) of the invention may represent a phosphine of the type $P(A^1R^{'1a})$ $(A^{'1}R^{'1b})(A^{''1}R^{'1c})$ or a phosphinamine of the type $(R^{'1a}A^1)$ $(R^{'1b}A^{'1})P$—$NH(R^{'2})$ or $(R^{'1a}A^1)(R^{'1b}A^{'1})P$—$NH$—$S(O)_2$ $(R^{'2})$, in which:

$A^1$, $A^{'1}$ and $A^{'''1}$, which may be mutually identical or different, are independently O, S, $NR^3$, or a single bond between the phosphorus atom and a carbon atom, the group $R^3$ is either a hydrogen atom or an alkyl group, which may or may not be cyclic, which may or may not be substituted and which may or may not contain heteroelements, or an aromatic group which may or may not be substituted and which may or may not contain heteroelements, the groups $R^{'1}$, i.e. $R^{'1a}$, $R^{'1b}$ and $R^{'1c}$, being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements, the group $R^{'2}$ is selected from alkyl groups which may or may not be cyclic, which may or may not be substituted and which may or may not contain heteroelements, and aromatic groups which may or may not be substituted and which may or may not contain heteroelements.

When the group $X^1$ is a carbon atom bonded to or forming part of at least one unsaturated, linear or cyclic alkyl group, $X^1$ and $L^1$ are advantageously bonded in a manner such that it forms an allyl fragment of a linear or cyclic alkyl to permit the formation of a π type nickel-allyl bond.

In accordance with the invention, the groups $R^1$ i.e. $R^{1a}$ and $R^{1b}$, which may be identical or different and which may or may not be bonded together, and the groups $R^{'1}$, i.e. $R^{'1a}$, $R^{'1b}$ and $R^{'1c}$, which may be mutually identical or different and which may or may not be bonded together, are independently selected from alkyl groups containing 1 to 15 carbon atoms and aromatic groups containing 5 to 20 carbon atoms, which may or may not be substituted and which may or may not contain heteroelements.

Preferably, the groups $R^1$, i.e. $R^{1a}$ and $R^{1b}$ which may be identical or different, which may or may not be bonded together, and the groups $R^{'1}$, i.e. $R^{'1a}$, $R^{'1b}$ and $R^{'1c}$, which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups, which may or may not be substituted and which may or may not contain heteroelements. In the case in which the groups $R^1$, i.e. $R^{1a}$ and $R^{1b}$, which may be identical or different, are bonded together, these groups may correspond to groups such as bis-phenyl or bis-naphthyl. In the case in which the groups $R^{'1}$, which may be identical or different, are bonded together, these groups may correspond to groups such as bis-phenyl or bis-naphthyl.

In accordance with the invention, the groups $R^2$ and the groups $R^{'2}$, which may be identical or different, are independently selected from alkyl groups containing 1 to 15 carbon atoms and aromatic groups containing 5 to 20 carbon atoms, which may or may not be substituted and which may or may not contain heteroelements.

Preferably, the groups $R^2$ and the groups $R'^2$, which may be identical or different, are independently selected from methyl, trifluoromethyl, ethyl, n-propyl, i-propyl, n-butyl, i-butyl, t-butyl, pentyl, cyclohexyl and adamantyl groups, which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-ditert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain heteroelements.

Preferably, the group $R^3$ is either a hydrogen atom or an alkyl group.

The complex of the invention may be prepared by bringing at least one ligand comprising the ligand fragment constituted by the atoms P, N, S and O with formula (1a), (1b) or (1c) as defined in accordance with the invention, into contact with at least one precursor of nickel with an oxidation number of (0), a precursor of the group $X^1$, a precursor of the group $L^1$ and optionally a precursor of the Lewis base group $L^2$. The presence of the Lewis base group $L^2$ is, for example, optional when a second equivalent of the ligand is employed. In this case, the ligand of the invention acts as a Lewis base. Advantageously, the precursors of the groups $X^1$ and $L^1$ may originate from a nickel (0) precursor. This is the case, for example, when the precursors of the groups $X^1$ and $L^1$ together form an unsaturated linear or cyclic alkyl. Preferably, said unsaturated linear or cyclic alkyl is a diene.

The complex of the invention may be prepared by bringing at least one ligand comprising the ligand fragment constituted by the atoms P, N, S and O with formula (1a), (1b) or (1c) as defined in accordance with the invention, into contact with at least one precursor of nickel with an oxidation number of (+II), in the presence of a precursor of the group $X^1$, a precursor of the group $L^1$, a reducing agent and optionally a precursor of the Lewis base group $L^2$. The presence of the Lewis base group $L^2$ is optional, for example, when a second equivalent of the ligand is employed. In this case, the ligand of the invention acts as a Lewis base.

In the case in which a nickel precursor with an oxidation number (+II) is used in the presence of a reducing agent, any agent resulting in the reduction of nickel which is known to the skilled person may be used. The reducing agent may be selected from $NaBH_4$, $LiAlH_4$, $AlEt_3$, Na, K, $KC_8$ and dihydrogen.

The preparation temperature for the complex of the invention may be in the range −80° C. to 130° C.

The complex of the invention may be prepared in the presence or absence of a solvent. Preferably, the preparation is carried out in the presence of a solvent. The preparation solvent may be selected from organic solvents, in particular from ethers, alcohols, chlorine-containing solvents and saturated, unsaturated, aromatic or non-aromatic, cyclic or non-cyclic hydrocarbons.

Preferably, the solvent is selected from hexane, cyclohexane, methylcyclohexane, heptane, butane or isobutane, monoolefins or diolefins preferably containing 4 to 20 carbon atoms, cycloocta-1,5-diene, benzene, toluene, ortho-xylene, mesitylene, ethylbenzene, dichloromethane, chlorobenzene, methanol, ethanol, pure or as a mixture, and ionic liquids. In the case in which the solvent is an ionic liquid, it is advantageously selected from the ionic liquids described in patents U.S. Pat. No. 6,951,831 B2 and FR 2 895 406 B1.

The complex of the invention comprises a nickel with an oxidation number (+I) or (+II), preferably a nickel with oxidation number (+II). The complexes of the invention may also form multi-nuclear aggregates.

When the nickel precursor has oxidation number (0), it may be selected from nickel(0) bis(cycloocta-1,5-diene), nickel(0) bis(cycloocta-1,3-diene), nickel(0) bis(cyclooctatetraene), nickel(0) bis(cycloocta-1,3,7-triene), bis(o-tolylphosphito) nickel(0) (ethylene), nickel(0) tetrakis(triphenylphosphite), nickel(0) tetrakis(triphenylphosphine) and nickel (0) bis(ethylene), used alone or as a mixture. Said nickel precursors may optionally be complexed with Lewis bases.

When the nickel precursor has oxidation number (+II), it may be selected from nickel (II) chloride, nickel chloride(II) (dimethoxyethane), nickel(II) bromide, nickel(II) (dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate, for example, nickel(II) phenates, nickel(II) acetate, nickel(II) trifluoroacetate, nickel(II) triflate, nickel (II) acetylacetonate, nickel(II) hexafluoroacetylacetonate, allylnickel(II) chloride, allylnickel(II) bromide, methallylnickel(II) chloride dimer, allylnickel(II) hexafluorophosphate, methallylnickel(II) hexafluorophosphate, biscyclopentadienyl nickel(II), bisallyl nickel(II) and bismethallyl nickel(II); in their hydrated or non-hydrated form, used alone or as a mixture. Said nickel precursors may optionally be complexed with Lewis bases.

We shall now present some examples of complexes with formula (I) in accordance with the invention as well as the operating conditions by means of which they are obtained. These examples are given by way of illustration and do not in any way limit the scope of the invention.

In the example of scheme 1, the addition of 2 equivalents of ligand L1 to one equivalent of nickel(0) bis(cycloocta-1,5-diene) ($Ni(COD)_2$) in 1,5-cyclooctadiene results in a complex with formula (I): C1. The preparation of this complex was carried out at a temperature in the range −40° C. to ambient temperature (AT) for 16 hours. The complex C1 was characterized in $^{31}P$ NMR by a broad singlet at 54 ppm.

Scheme 1

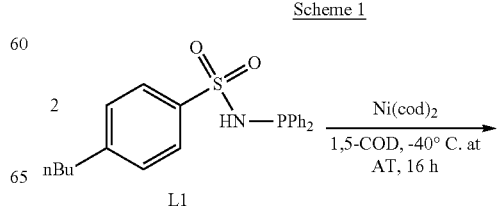

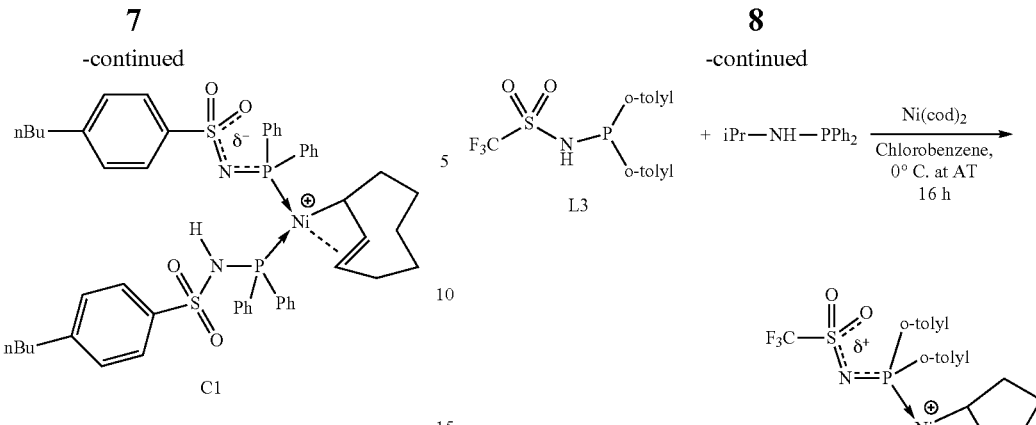

Another type of complex with formula (I) in accordance with the invention was prepared by addition of one equivalent of ligand L2 or L3 and one equivalent of N-(diphenylphosphino)isopropylamine ((iPr)NHPPh₂) or N-(diphenylphosphino)-n-propylamine ((nPr)NHPPh₂) to one equivalent of nickel(0) bis(cycloocta-1,5-diene) in toluene or chlorobenzene. The complexes C2, C3, C4 and C5 were obtained at a temperature in the range 0° C. to 50° C. after a period of 1 to 16 hours (Scheme 2). The complexes were characterized in $^{31}$P NMR by two doublets with a coupling constant of the order of 30 Hz.

The bisnaphthol group in scheme 3 illustrates two complexes with formula (I) in which the substituents $R^{1a}$ and $R^{1b}$ are bonded together, A=O and in which the group $R^2$ is a 4-n-butyl phenyl (C6) group or a —CF₃ (C7) group. The complexes C6 and C7 were prepared by addition of one equivalent of ligand L4 or L5 (represented here with one equivalent of Et₃N) respectively and one equivalent of trimethylphosphine to one equivalent of nickel(0) bis(cycloocta-1,5-diene) in chlorobenzene. The complexes were obtained at the end of 3 hours at ambient temperature (AT).

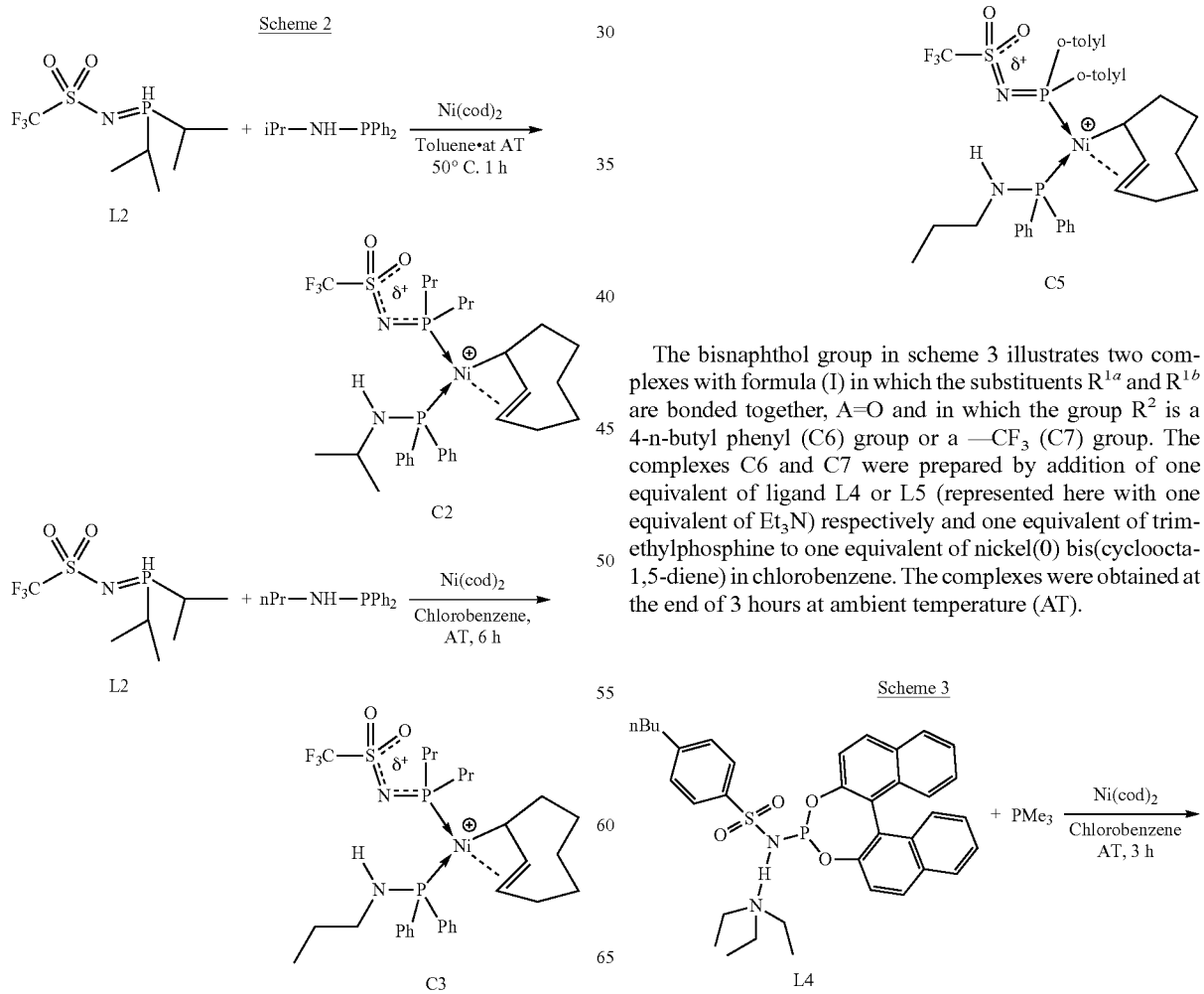

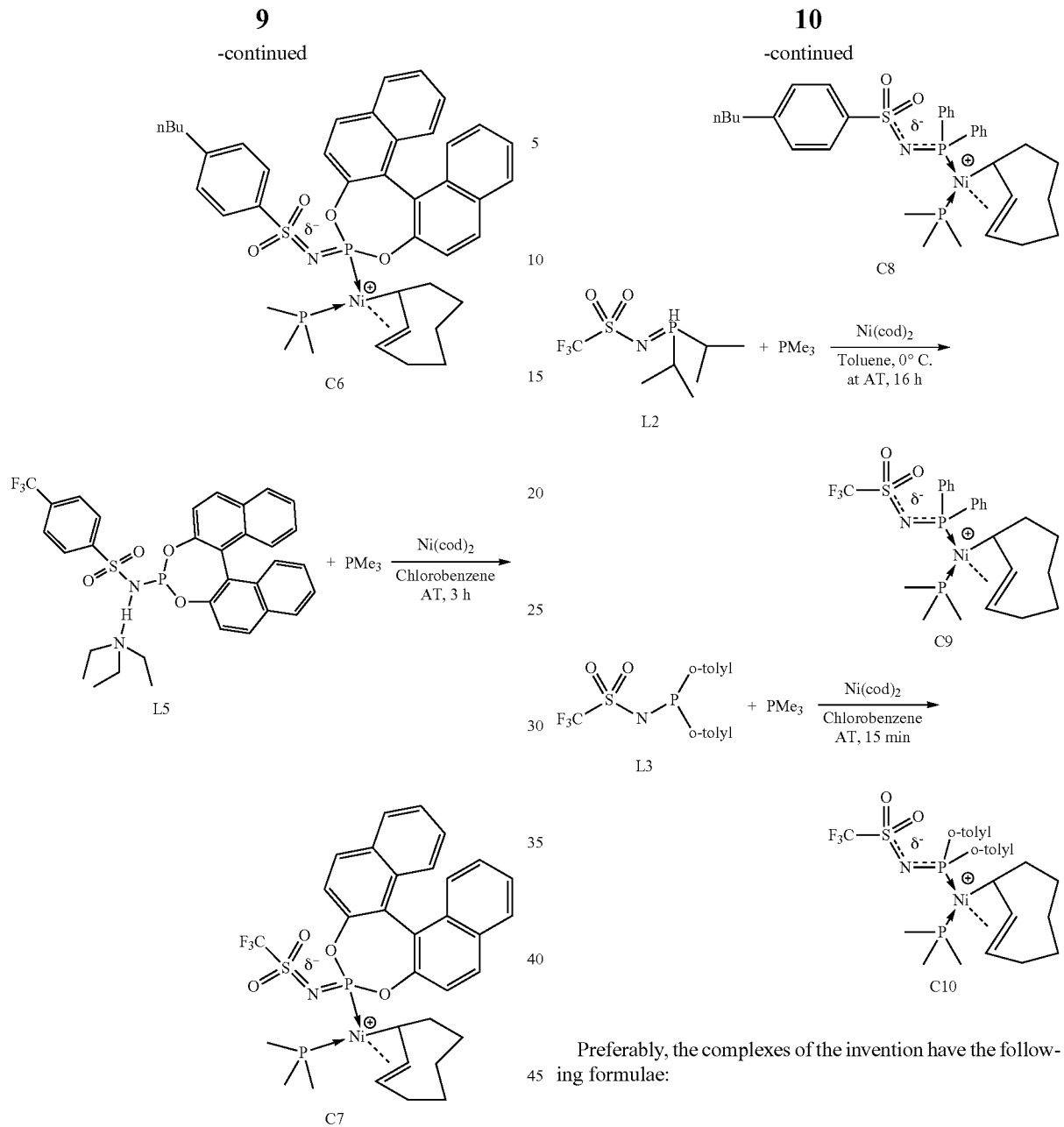
Similar complexes C8, C9 and C10, with a trimethylphosphine ligand were obtained under the same conditions with the respective ligands L1, L2 and L3 (scheme 4). These complexes were characterized in $^{31}$P NMR by two doublets with a coupling constant of the order of 30 Hz.
Scheme 4
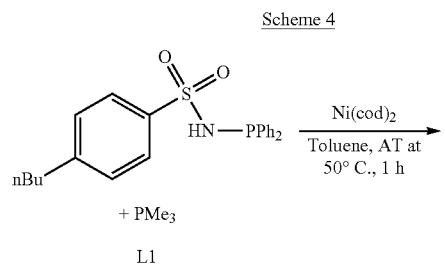
Preferably, the complexes of the invention have the following formulae:
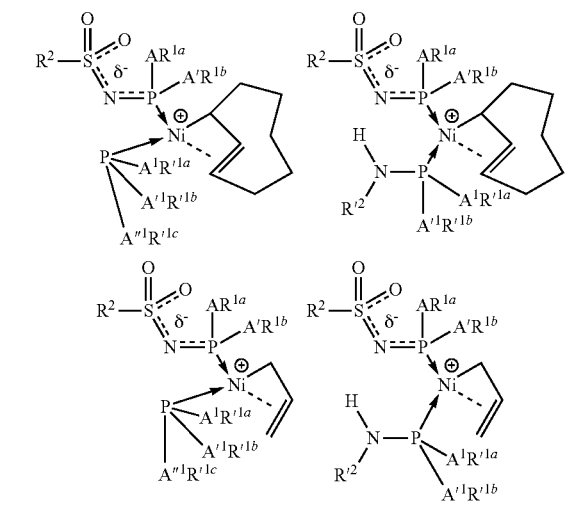

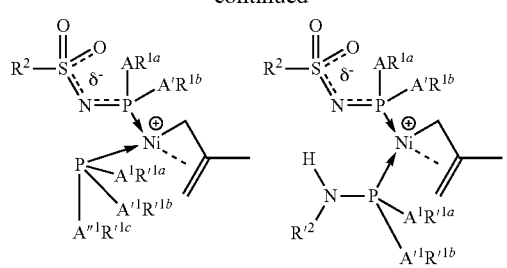 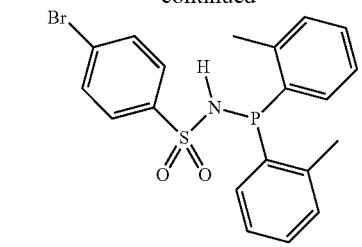

in which the nickel has oxidation number (+II), δ⁻ represents the delocalisation of the negative charge over the ligand fragment constituted by the atoms P, N, S and O and A, A', A¹, A'¹, A''¹, $R^{1a}$, $R^{1b}$, $R'^{1a}$, $R'^{1b}$, $R'^{1c}$, $R^2$ and $R'^2$ have the meanings given in the context of the invention.

A non-exhaustive list of ligands which may be suitable for the preparation of the complexes of the invention is represented below. The ligands here are represented in their limiting forms 1a) and 1b).

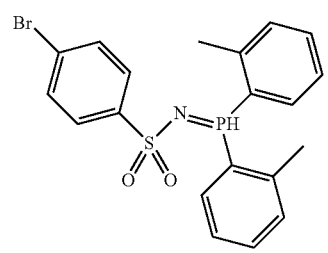 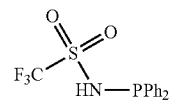

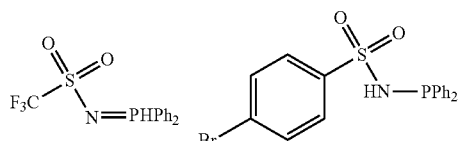

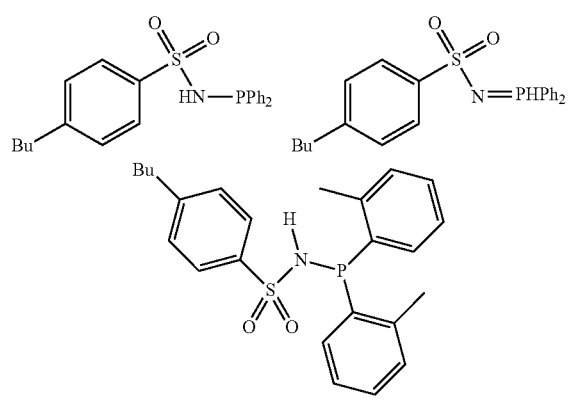

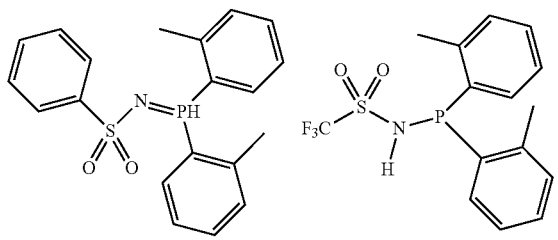

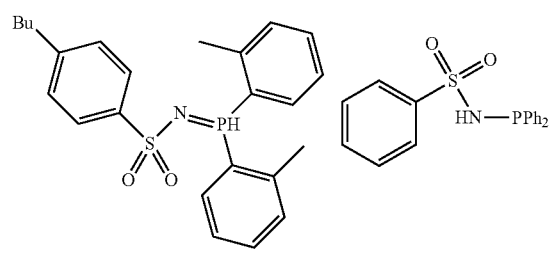

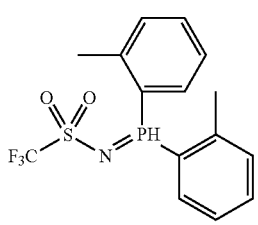

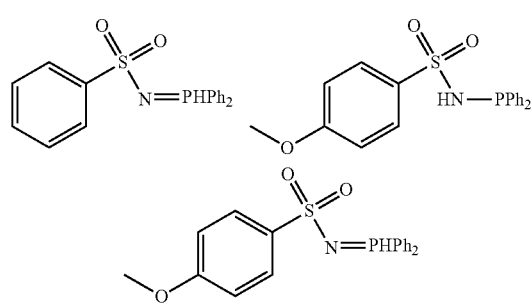

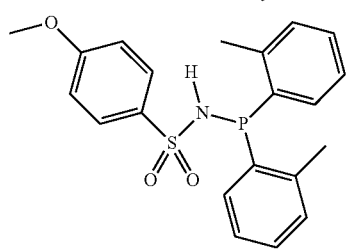

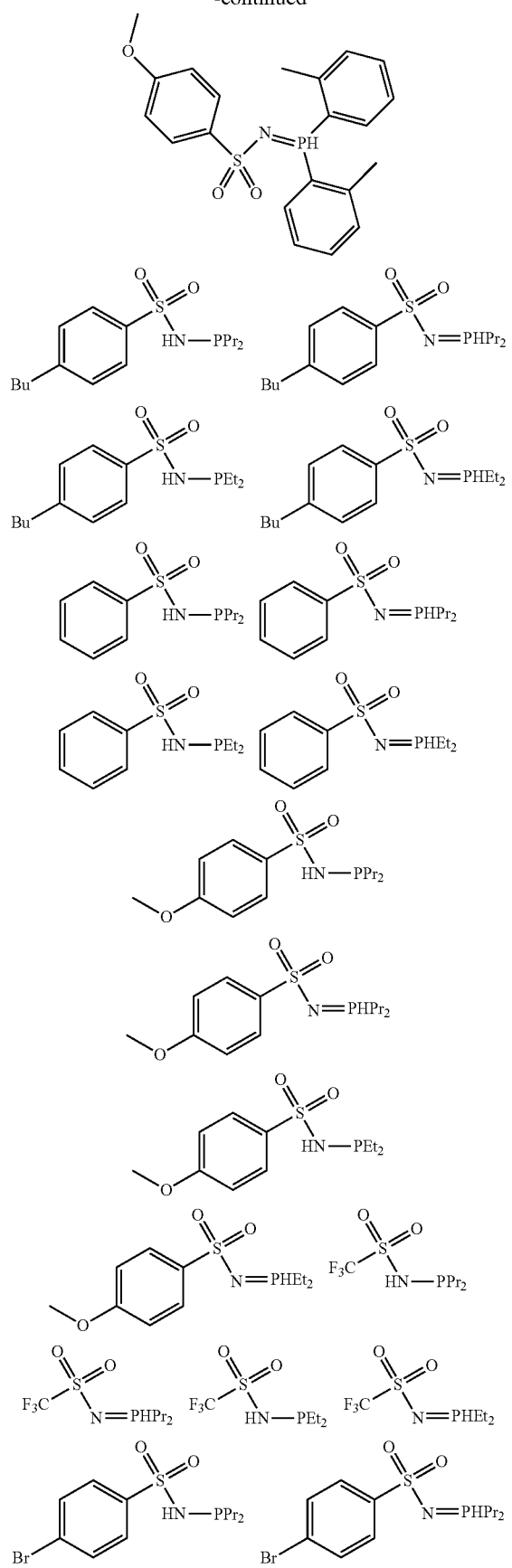
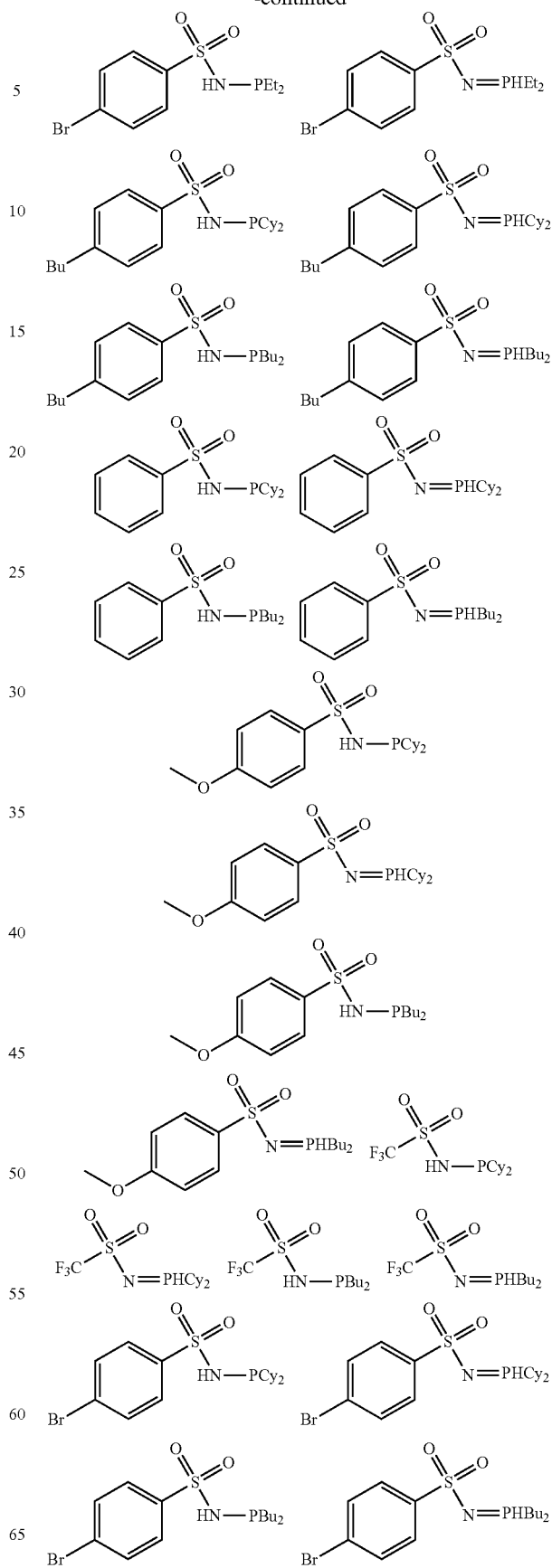

-continued

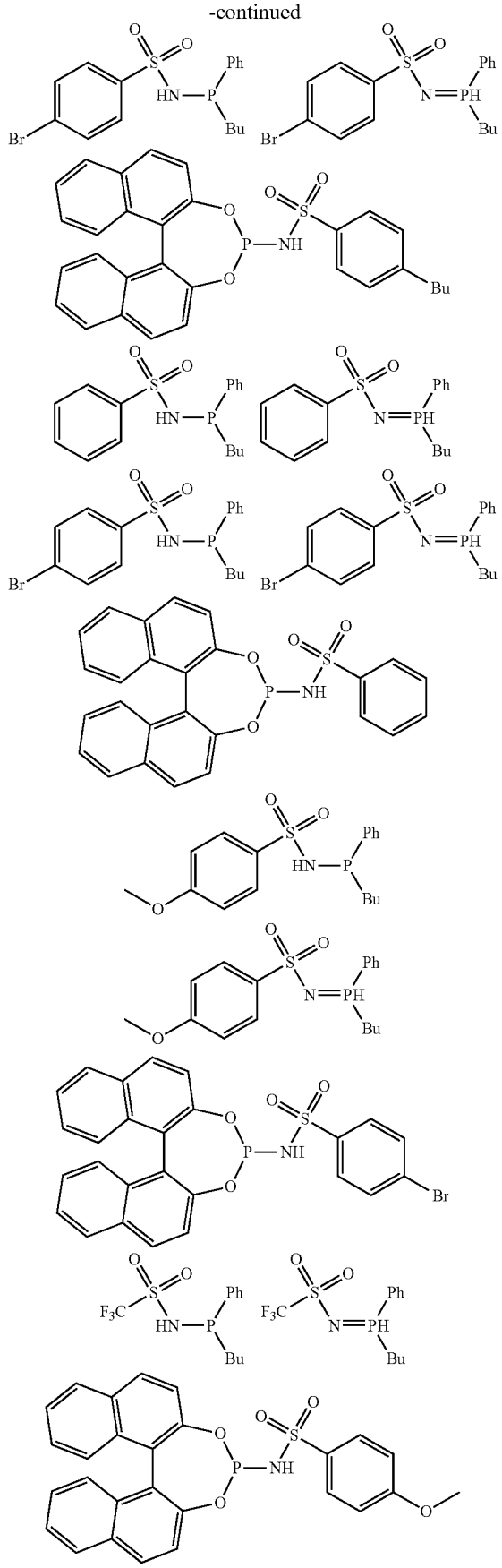

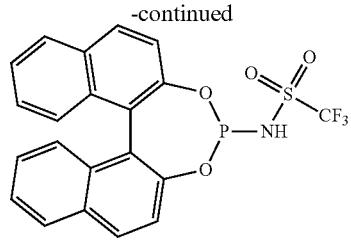

Use of Complexes with Formula (I) in a Chemical Transformation Reaction

The nickel-based complexes with formula (I) of the invention may be used as a catalyst in a chemical transformation reaction such as a hydrogenation, hydroformylation, cross coupling or olefin oligomerization reaction. In particular, these complexes are used in a process for the oligomerization of a feed of olefins advantageously containing 2 to 10 carbon atoms.

Preferably, the oligomerization process is a process for the dimerization of ethylene to 1-butene.

The nickel complex with formula (I) of the invention may be used in the form of a catalytic composition, mixed with a compound known as an activating agent. Said activating agent is advantageously selected from the group formed by tris(hydrocarbyl)aluminium compounds, chlorine-containing or bromine-containing hydrocarbylaluminium compounds, aluminium halides, aluminoxanes, organo-boron compounds, and organic compounds which are capable of donating or accepting a proton, used alone or as a mixture.

The tris(hydrocarbyl)aluminium compounds, the chlorine-containing or bromine-containing hydrocarbylaluminium compounds and the aluminium halides preferably have the general formula $Al_xR_yW_z$, in which R represents a monovalent hydrocarbon radical containing, for example, up to 12 carbon atoms such as alkyl, aryl, aralkyl, alkaryl or cycloalkyl, W represents a halogen atom selected from chlorine and bromine, for example, W preferably being a chlorine atom, x takes the value of 1 to 2, y and z taking a value of 0 to 3. Examples of compounds of this type which may be mentioned are ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), diethylaluminium chloride ($Et_2AlCl$), trimethylaluminium, tributylaluminium, tri-n-octylaluminium and triethylaluminium ($AlEt_3$).

In the case in which said activating agent is selected from aluminoxanes, said activating agent is advantageously selected from methylaluminoxane (MAO), ethylaluminoxane and modified methylaluminoxanes (MMAO). These activating agents may be used alone or as a mixture.

Preferably, said activating agent C is selected from dichloroethylaluminium ($EtAlCl_2$) and methylaluminoxane (MAO).

In the case in which said activating agent is selected from organoboron compounds, said activating agent is preferably selected from Lewis acids of the tris(aryl)borane type, such as tris(perfluorophenyl)borane, tris(3,5-bis(trifluoromethyl)phenyl)borane, tris(2,3,4,6-tetrafluorophenyl)borane, tris(perfluoronaphtyl)borane, tris(perfluorobiphenyl)borane and their derivatives and (aryl)borates associated with a triphenylcarbenium cation, or a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate.

In the case in which said activating agent is selected from organic compounds which are susceptible of donating a proton, said activating agent is preferably selected from acids with formula HY in which Y represents an anion.

In the case in which said activating agent is selected from organic compounds which are susceptible of accepting a proton, said activating agent is preferably selected from Bronsted bases.

The solvent for the oligomerization process may be selected from organic solvents, preferably from ethers, alcohols, chlorine-containing solvents and saturated, unsaturated, aromatic or non-aromatic, cyclic or non-cyclic hydrocarbons. In particular, said solvent is selected from hexane, cyclohexane, methylcyclohexane, heptane, butane or isobutane, monoolefins or diolefins preferably containing 4 to 20 carbon atoms, cycloocta-1,5-diene, benzene, toluene, ortho-xylene, mesitylene, ethylbenzene, dichloromethane, chlorobenzene, methanol and ethanol, pure or as a mixture, and ionic liquids. In the case in which said reaction solvent is an ionic liquid, it is advantageously selected from the ionic liquids described in patents U.S. Pat. No. 6,951,831 B2 and FR 2 895 406 B1.

Oligomerization is defined as the transformation of a monomer unit into a compound or mixture of compounds with general formula $C_pH_{2p}$, with $4 \leq p \leq 80$, preferably with $4 \leq p \leq 50$, more preferably with $4 \leq p \leq 26$ and highly preferably with $4 \leq p \leq 14$.

The olefins used in the oligomerization process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) such as those found in "cuts" obtained from oil refining processes such as catalytic cracking or steam cracking.

Preferably, the olefin used in the oligomerization process is ethylene.

Said olefins may be obtained from non-fossil sources such as biomass. As an example, the olefins used in the oligomerization process or dimerization process of the invention may be produced from alcohols, in particular by dehydration of alcohols.

The concentration of nickel in the catalytic solution is advantageously in the range $1 \times 10^{-8}$ to 1 mol/L, and preferably in the range $1 \times 10^{-6}$ to $1 \times 10^{-2}$ mol/L.

The oligomerization process is advantageously operated at a total pressure in the range between atmospheric pressure and 20 MPa, preferably in the range 0.1 to 8 MPa, and at a temperature in the range −40° C. to +250° C., preferably in the range −20° C. to 150° C.

The heat generated by the reaction can be eliminated using any means known to the skilled person.

The oligomerization process may be carried out in a closed system, in a semi-open system or continuously, with one or more reaction stages. Vigorous stirring is advantageously carried out to ensure good contact between the reagent or reagents and the catalytic system.

The oligomerization process may be carried out discontinuously. In this case, a selected volume of the solution comprising the complex of the invention is introduced into a reactor provided with the usual stirring, heating and cooling devices.

The oligomerization process may also be carried out in a continuous manner. In this case, the solution comprising the complex of the invention is injected at the same time as the olefin into a reactor stirred using conventional mechanical means or by external recirculation, maintaining the desired temperature.

The catalytic composition is destroyed by any usual means known to the skilled person, then the reaction products as well as the solvent are separated, for example by distillation. The olefin which has not been transformed may be recycled to the reactor.

The process of the invention may be carried out in a reactor with one or more reaction stages in series, the olefinic feed and/or the catalytic composition, having been pre-conditioned, being introduced continuously, either into the first stage or into the first and any other of the stages. At the reactor outlet, the catalytic composition may be deactivated, for example by injecting ammonia and/or an aqueous solution of sodium hydroxide and/or an aqueous solution of sulphuric acid. The unconverted olefins and any alkanes present in the feed are then separated from the oligomers by distillation.

The products of the present process may find an application, for example, as fuel components for automobiles, as feeds in a hydroformylation process for the synthesis of aldehydes and alcohols, as components for the chemicals, pharmaceuticals or perfumery industry and/or as feeds in a metathesis process for the synthesis of propylene, for example.

The following examples illustrate the invention without limiting its scope. The notation "Cy" represents the cyclohexyl group.

Example 1

Synthesis of N-(diphenylphosphino)isopropylamine ((iPr)NHPPh2) using the method described in WO2008/077908.

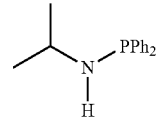

Isopropylamine (1.8 mL, 22.3 mmol, 2 eq(equivalents)) and triethylamine (4.66 mL, 33.4 mmol, 3 eq.) were placed in a Schlenk flask with 10 mL of tetrahydrofuran (THF). Chlorodiphenylphosphine (2 mL, 11.14 mmol, 1 eq.) was added to this mixture drop by drop. The mixture was stirred for 10 minutes (min) at ambient temperature and the precipitate formed was filtered. The filtrate was vacuum dried to produce a colourless oil. Trituration of the oil in pentane produced a white powder. This powder was rinsed with 2×10 mL of pentane. 2.1 g of a white powder was isolated, i.e. a yield of 75%. The pure product was obtained by distillation of the solid under low pressure. The product was characterized by $^{31}P$ NMR spectroscopy ($C_6D_6$), $^1H$ NMR ($C_6D_6$) and $^{13}C$ NMR ($C_6D_6$). $^{31}P$ NMR ($C_6D_6$): 34.94.

Synthesis of N-(diphenylphosphino)-n-propylamine ((nPr)NHPPh$_2$) using the method described in WO2008/077908.

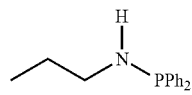

n-propylamine (3 mL, 2.17 g, 36.7 mmol, 3 eq.) was mixed with THF (10 mL). Chlorodiphenylphosphine (2 mL, 2.46 g, 11.1 mmol, 1 eq.) was added to this mixture drop by drop.

After 10 minutes of stirring at ambient temperature, the mixture was filtered and the liquid phase was collected. The liquid phase was evaporated off under reduced pressure to produce a pale yellow oil (isolated: 2.3 g, 85%).

Synthesis of Ligands L1, L2, L4, L5

The synthesis of ligands L1, L2, L4 and L5 was carried out using the method described in the literature: F. G. Terrade, *Eur. J. Inorg. Chem.* 2014, 1826-1835.

Synthesis of METAMORPhos (o-tolyl) ligand L3

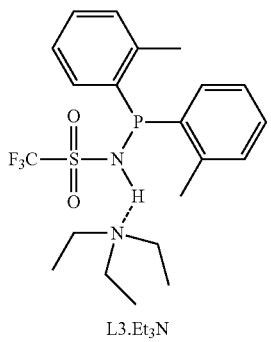

L3.Et$_3$N

Trifluoromethane sulphonamide (2.4 g, 16 mmol, 1 eq.) and triethylamine (4.2 g, 40 mmol, 2.6 eq., 6 mL) were dissolved in 30 mL of THF. Di(o-tolyl)chlorophosphine was dissolved with 10 mL of THF in a second Schlenk flask. The solution of chlorophosphine (4 g, 16 mmol, 1 eq.) in 10 mL of THF was added drop by drop to the solution of sulphonamide to produce a white precipitate. After 20 min, the mixture was filtered and the solid was rinsed twice with 10 mL of THF. The liquid phase was evaporated off under vacuum to obtain a colourless oil. 20 mL of diethylether was added to said oil to precipitate a white powder. The powder was rinsed three times with 5 mL of diethylether. After drying under vacuum, 2.52 g of powder was obtained, i.e. a yield of 68%.

The product was characterized by $^{31}$P{$^1$H} NMR (C$_6$D$_6$), $^{31}$P NMR (C$_6$D$_6$), $^1$H NMR (C$_6$D$_6$) and $^{13}$C NMR (C$_6$D$_6$) spectroscopy.

$^{31}$P NMR (C$_6$D$_6$): 15.77 (s, PH form 12%); 22.62 (broad s., NH-NEt$_3$ form, 88%).

Synthesis of Complex C1

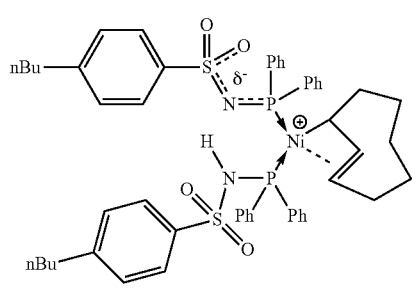

The ligand L1 (4-nBu-Bz-SO$_2$—NH—PPh$_2$, 397 mg, 1 mmol, 2 eq.) and Ni(COD)$_2$ were dissolved in dry 1,5-cy-clooctadiene (10 mL) and the mixture was stirred for 16 hours (h) until the phosphorus NMR signal of the ligand disappeared. The solvent was evaporated to provide a dark green oil. This oil was triturated with pentane several times in order to eliminate the traces of cyclooctadiene. The oil was then extracted with a heptane/toluene mixture (4:1) and the fractions of solvent were combined and evaporated to provide an orange solid in the form of a powder. The powder was washed twice with 10 mL of pentane to obtain an orange powder (131 mg, isolated yield: 27%).

$^{31}$P NMR (C$_6$D$_6$): 54.06

Elemental analysis. Found (Theoretical): C: 64.17 (64.94); H: 6.64 (6.29); N: 3.15 (2.91).

Synthesis of Complex C2

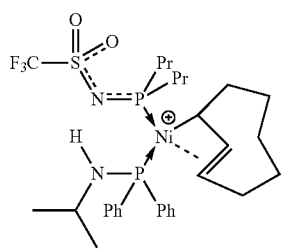

The ligand L2 (F$_3$C—SO$_2$—N=P(iPr)$_2$H, 395 mg, 1.5 mmol, 1 eq.), N-(diphenylphosphino)isopropylamine (365 mg, 1.5 mmol, 1 eq.) and Ni(COD)$_2$ (413 mg, 1.5 mmol, 1 eq.) were placed in a Schlenk flask and dissolved in 30 mL of toluene to which 4 drops of 1,5-cyclooctadiene had been added. The solution was then heated to 50° C. for 20 mn. The solvents were evaporated to provide an oily solid. This solid was triturated in pentane (10 mL), then the pentane was removed with a syringe. The operation was carried out once more to provide a solid, then washed with 3×10 mL of pentane. The powder was dissolved in toluene and filtered through a disc syringe to eliminate the solid residues, then the filtrate obtained was evaporated. The powder obtained was triturated in pentane then washed with 2×10 mL of pentane and finally dried under vacuum. A yellow powder was obtained (isolated yield: 574 mg, 57%).

$^{31}$P NMR (C$_6$D$_6$): 85.76 (d, J=30.9 Hz); 60.22 (d, J=31.3 Hz)

Elemental analysis. Found (Theoretical): C, 42.39 (42.54); H: 7.26 (7.14); N: 2.68 (2.76).

Synthesis of Complex C3

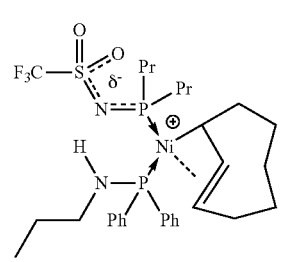

The ligand L2 ($F_3C$—$SO_2$—N=P(iPr)$_2$H, 265 mg, 1 mmol, 1 eq.), N-(diphenylphosphino)-n-propylamine (243 mg, 1 mmol, 1 eq.) and Ni(COD)$_2$ (275 mg, 1 mmol, 1 eq.) were placed in a Schlenk flask and dissolved in 20 mL of chlorobenzene to which 0.5 mL of 1,5-cyclooctadiene had been added. The solution was stirred for 6 h at ambient temperature, then the solvent was evaporated off under reduced pressure to provide a dark yellow solid. This solid was triturated then washed with 2×10 mL of pentane. The powder was then dried under vacuum and suspended in 5 mL of toluene. The solvent was evaporated off and the operation was carried out once again to provide a powder which was only very slightly soluble in toluene. The powder was then dissolved in 5 mL of dichloromethane and the solution was filtered through a 0.2 μm disc syringe to eliminate the insolubles. The dichloromethane was evaporated off, then 5 mL of toluene was added which was in turn evaporated off under vacuum. A canary-yellow powder was obtained (isolated: 325 mg, 47%).

$^{31}$P NMR (CD$_2$Cl$_2$): 64.54 (d, $^2J_{PP}$=31 Hz); 92.16 (d, $^2J_{PP}$=31 Hz).

Synthesis of Complex C4

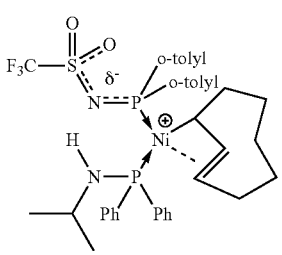

C4

The ligand L3 (463 mg, 1 mmol, 1 eq.), N-(diphenylphosphino)isopropylamine (244 mg, 1 mmol, 1 eq.) and Ni(COD)$_2$ (275 mg, 1 mmol, 1 eq.) were dissolved in 20 mL of chlorobenzene at 0° C. The mixture was stirred at ambient temperature for 16 h to produce a dark solution. The solvent was evaporated off under reduced pressure to produce a dark oil. The oil was triturated in diethyl ether (10 mL), then the solvent was removed with the aid of a syringe. The operation was carried out another two times, which allowed the production of a yellow powder which was washed with ether at 0° C. until the ether phase was no longer dark. The solid was then dried under vacuum to produce the product (190 mg isolated: 25% yield).

$^{31}$P NMR (C$_6$D$_6$): 52.13 (d, $^2J_{PP}$=23.1 Hz); 62.82 (d, $^2J_{PP}$=23.3 Hz);

Elemental analysis. Found (Theoretical):C: 51.62 (59.46); 5.25 (5.88); 3.22 (3.63).

Synthesis of Complex C5

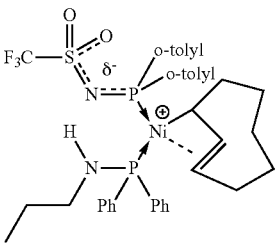

C5

The ligand L3 (463 mg, 1 mmol, 1 eq.), N-(diphenylphosphino)-n-propylamine (243 mg, 1 mmol, 1 eq.) and Ni(COD)$_2$ (275 mg, 1 mmol, 1 eq.) were dissolved in 15 mL of chlorobenzene at 0° C. The mixture was stirred at ambient temperature for 4 h to provide a dark brown solution. The solvent was evaporated off under reduced pressure to provide a dark oil. The oil was triturated and washed with pentane (7×5 mL), which resulted in the formation of a dark yellow solid which was dried under vacuum. This solid was then washed with diethyl ether at 0° C. (3×10 mL). The ether was evaporated off under reduced pressure, then the powder was suspended in 5 mL of toluene which was evaporated off under reduced pressure. The operation was carried out once more and produced a pale yellow powder (isolated 280 mg, 36%).

$^{31}$P NMR (CD$_2$Cl$_2$): 52.33 (d, $^2J_{PP}$=24.7 Hz); 65.09 (d, $^2J_{PP}$=24.5 Hz).

Synthesis of Complex C6

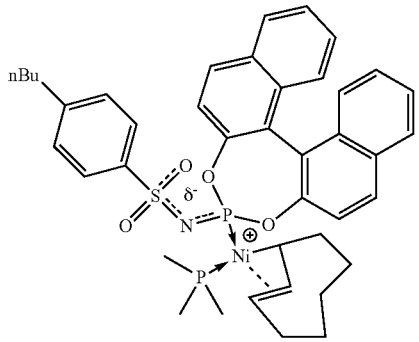

C6

The ligand L4 (4-nBu-C$_6$H$_4$—SO$_2$—NH—P((R)-Binol) isolated with one equivalent of trimethylamine (53 mg, 0.1 mmol, 1 eq.) and Ni(COD)$_2$ (28 mg, 0.1 mmol, 1 eq.) were dissolved in chlorobenzene (3 mL). A solution of trimethylphosphine (10% in toluene, 10 μL, 0.1 mmol, 1 eq.) was added to this solution. The solution rapidly turned brown and was stirred for 3 h at ambient temperature. The solvent was evaporated off, producing a brown solid which was triturated and washed with 3×5 mL of pentane. The solid was dried to give a yellow powder: isolated yield 35%. Two diastereoisomers (a) and (b) were formed in a ratio of 1:1.

$^{31}$P NMR (C$_6$D$_6$): (a) −13.4 (d, $^2J_{PP\text{-}cis}$=36 Hz) and 155.3 (d, $^2J_{PP\text{-}cis}$=36 Hz)
(b) −12.7 (d, $^2J_{PP\text{-}cis}$=39 Hz) and 156.2 (d, $^2J_{PP\text{-}cis}$=39 Hz).

Synthesis of Complex C7

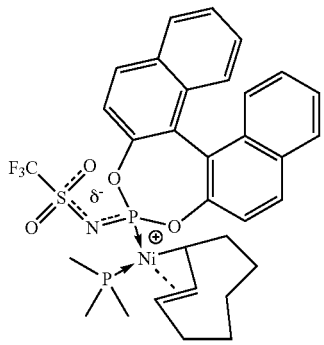

The ligand L5 (F$_3$C—NH—P((R)-Binol, isolated with one equivalent of trimethylamine (46 mg, 0.1 mmol, 1 eq.) and Ni(COD)$_2$ (28 mg, 0.1 mmol, 1 eq.) were dissolved in chlorobenzene (3 mL). A solution of trimethylphosphine (10% in toluene, 10 µL, 0.1 mmol, 1 eq.) was added to this solution. The solution rapidly turned brown and was stirred for 3 h at ambient temperature. The solvent was evaporated off to provide a brown solid which was triturated and washed with 3×5 mL of pentane. The solid was dried to provide a yellow powder: isolated yield 35%. Two diastereoisomers (a) and (b) were formed in a ratio of 1:1.

$^{31}$P NMR (C$_6$D$_6$): (a) −14.2 (d, $^2J_{PP\text{-}cis}$=33 Hz) and 157.6 (d, $^2J_{PP\text{-}cis}$=33 Hz)

(b) −13.6 (d, $^2J_{PP\text{-}cis}$=36 Hz) and 158.0 (d, $^2J_{PP\text{-}cis}$=36 Hz).

Synthesis of Complex C8

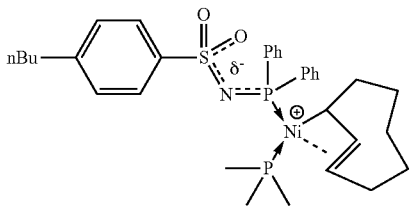

The ligand L1 (4-nBu-C$_6$H$_4$—SO$_2$—NH—PPh$_2$, 390 mg, 1 mmol, 1 eq) and trimethylphosphine (1M solution in toluene, 1 mL, 1 mmol, 1 eq.) were placed in a Schlenk flask and dissolved in 30 mL of toluene. Ni(COD)$_2$ (270 mg, 1 mmol, 1 eq) was dissolved in 20 mL of toluene in another Schlenk flask. The two solutions were cooled in a water/ice bath and the solution containing the phosphines was added to the nickel solution via a cannula. After addition, the mixture was allowed to heat up to ambient temperature and stirred for 20 min. Finally, it was heated to 60° C. for 1 h to provide a dark brown liquid. The solvent was then evaporated off to provide an orange powder. The solid was washed with pentane to provide an orange powder: isolated yield 36%.

$^{31}$P NMR (C$_6$D$_6$): 60.25 (d, $^2J_{PP\text{-}cis}$=26.7 Hz); −0.11 (d, $^2J_{PP\text{-}cis}$=26.7 Hz)

Elemental analysis. Found (Theoretical): C, 61.67 (61.69); H: 6.87 (7.08); N: 2.27 (2.19).

Synthesis of Complex C9

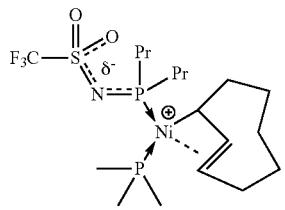

The ligand L2 (F$_3$C—SO$_2$—N=P(iPr)$_2$H, 106 mg, 0.4 mmol, 1 eq) and trimethylphosphine (1M solution in toluene, 0.5 mL, 0.5 mmol, 1.25 eq.) were placed in a Schlenk flask with 30 mL of toluene. Ni(COD)$_2$ was dissolved in 20 mL of toluene in another Schlenk flask. The two solutions were cooled in a water/ice bath and the solution containing the phosphines was added to the nickel solution. The solution was stirred for 16 h. Next, the solvent was evaporated off to provide a yellow powder which was triturated then washed with 3×10 mL of pentane then dried under vacuum.

$^{31}$P NMR (C$_6$D$_6$): 86.8 ppm (d, P(iPr)$_2$ $^2J_{PP}$=31.05 Hz); −11.4 ppm (d, P(Me)$_3$ $^2J_{PP}$=31.45 Hz).

Synthesis of Complex C10

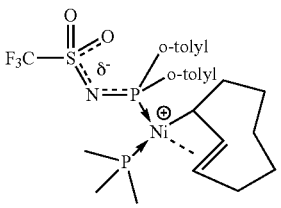

The ligand L3 (463 mg, 1 mmol, 1 eq.) and Ni(COD)$_2$ (275 mg, 1 mmol, 1 eq.) were dissolved in 20 mL of chlorobenzene. Trimethylphosphine (1M in toluene, 1 mL, 1 mmol, 1 eq.) was added to this solution. The mixture was stirred for 15 minutes, resulting in a dark solution. The solvent was then eliminated under reduced pressure to provide a dark solid. The solid was triturated with 20 mL of pentane to provide a yellow powder and a violet-coloured solvent. The solid was the rinsed with pentane until the violet colour had disappeared. The solid was dried under vacuum to provide a yellow powder: isolated yield 53%.

$^{31}$P NMR (C$_6$D$_6$): −15.10 (d, $^2J_{PP}$=25.8 Hz); 54.75 (d, $^2J_{PP}$=25.8 Hz).

Elemental analysis. Found (Theoretical): C: 51.57 (51.68); H: 5.89 (6.00); N: 2.47 (2.33).

Synthesis of Complex C11

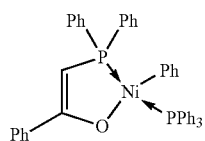

The reference complex C11 was synthesized as described in the literature (Organometallics 1986, 5, 2356-2359) and the characterizations were in agreement with the expected product.

Example 2

Oligomerization of Ethylene

The ethylene oligomerization reaction was evaluated with the complexes C1, C2, C4, C8 and C9 (10 µmoles), with the complex C11 as a comparative example. The results obtained are reported in Table 1.

The 250 mL reactor was dried under vacuum at 130° C. for 2 hours then pressurized with 0.5 MPa of ethylene. The temperature was dropped to 20° C., then the excess pressure of ethylene was evacuated to obtain 0.1 MPa. The solvent was added (45 mL of toluene) and the internal temperature was set (40° C. or 80° C.). Once the internal temperature had stabilized, the complex was introduced (10 µmol in 5 mL of toluene). Next, the reactor was pressurized with 3 MPa of ethylene. Stirring (1000 rpm) was commenced (t=0). After the pre-set reaction time, the mixture was cooled to 30° C. with stirring, the reactor was depressurized and the liquid and gas phases were analysed by gas phase chromatography (GC).

The productivity ($g_{oligo}/(g_{Ni} \cdot h)$) is expressed as the mass of oligomers produced (in grams) per unit mass of nickel employed per hour.

present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding French Application No. 14/53817, filed Apr. 28, 2014 are incorporated by reference herein.

The invention claimed is:

1. A nickel-based complex having formula (I)

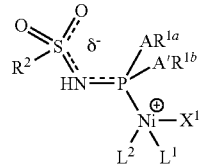

in which
the atoms P, N, S, O constitute a ligand fragment,
A and A', which may be identical or different, are independently O, S, $NR^3$ or a single bond between the phosphorus atom and a carbon atom of $R^{1a}$ or $R^{1b}$,
the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements,
the groups $R^1$, represented in the formula by $R^{1a}$ and $R^{1b}$, with $R^{1a}$ and $R^{1b}$ being mutually identical or

TABLE 1

Oligomerization of ethylene with different complexes (30 bar of ethylene)

| Complex | Temperature | Mass of oligomers (g) | Reaction time (min) | Productivity $g_{oligo}/(g_{Ni} \cdot h)$ | Product distribution (by wt)[a] | | | 1-butene[b] | 1-hexene |
|---|---|---|---|---|---|---|---|---|---|
| | | | | | $C_4$ | $C_6$ | $C_8^+$ | | |
| C1 | 40° C. | 4.4 | 90 | 4956 | 92.7 | 6.6 | 0.7 | 99.7 | 95.5 |
| C1 | 80° C. | 5.8 | 90 | 6588 | 86.2 | 12.1 | 1.7 | 99.4 | 91.9 |
| C2 | 40° C. | 10.2 | 90 | 11632 | 35.1 | 28.1 | 36.8 | 99.7 | 98.8 |
| C4 | 40° C. | 23.9 | 90 | 27187 | 86.3 | 11.9 | 1.8 | 98.0 | 81.7 |
| C8 | 80° C. | 7.6 | 90 | 8601 | 86.4 | 12.1 | 1.5 | 98.3 | 90.5 |
| C9 | 40° C. | 5.8 | 90 | 6638 | 37.4 | 28.8 | 33.8 | 99.7 | 99.0 |
| C11 (50 µmol) | 40° C. | 32 | 130 | 5218 | 1.2 | 2.4 | 96.4 | 76.7 | 96.4 |

[a]Determined by GC (percentage by weight of $C_4$, $C_6$ and $C_8^+$ with respect to all of the oligomers).
[b]Percentage by weight of 1-butene in the $C_4$ cut.

The above examples demonstrate that the complexes of the invention exhibit good activity in the oligomerization of ethylene.

Without further elaboration, it is believed that one skilled in the art can, using the preceding description, utilize the different and which may or may not be bonded together, are selected from alkyl groups which may or may not be cyclic, which may or may not be substituted and which may or may not contain heteroelements, and aromatic groups which may or may not be substituted and which may or may not contain heteroelements, the group $R^2$ is selected from alkyl groups which may or may not be cyclic, which may or may not be substituted and which may or may not contain heteroelements, and aromatic groups which may or may not be substituted and which may or may not contain heteroelements, $L^1$ and $L^2$, which may be identical or different, represent a Lewis base, $X^1$ is a carbon atom bonded to or forming part of at least one alkyl group, which may or may not be cyclic, which may or may not be unsaturated, which may or may not be substituted and which may or may not contain heteroelements, and an aromatic group which may or may not be substituted and which may or may not contain heteroelements, $L^1$, $L^2$ and $X^1$ are such that the oxidation number of the nickel is respected, and $\delta^-$ represents the delocalisation of the negative charge over the ligand fragment constituted by the atoms P, N, S and O.

2. The complex according to claim 1, in which $L^2$ represents a phosphine of the formula $P(A^1R'^{1a})(A'^1R'^{1b})(A'''R'^{1c})$ or a phosphinamine of the formula $(R'^{1a}A'^1)(R'^{1b}A'^1)P-NH(R'^2)$ or $(R'^{1a}A^1)(R'^{1b}A'^1)P-NH-S(O)_2(R'^2)$, in which:

$A^1$, $A'^1$ and $A'''^1$, which may be identical or different, are independently O, S, $NR^3$ or a single bond between the phosphorus atom and a carbon atom of $R'^{1a}$, $R'^{1b}$, or $R'^{1c}$, the group $R^3$ is either a hydrogen atom or an alkyl group, which may or may not be cyclic, which may or may not be substituted and which may or may not contain heteroelements, or an aromatic group which may or may not be substituted and which may or may not contain heteroelements, the groups $R'^1$, i.e. $R'^{1a}$, $R'^{1b}$ and $R'^{1c}$, being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements, the group $R'^2$ is selected from alkyl groups which may or may not be cyclic, which may or may not be substituted and which may or may not contain heteroelements, and aromatic groups which may or may not be substituted and which may or may not contain heteroelements.

3. The complex according to claim 1 in which, when $X^1$ is a carbon atom bonded to or forming part of at least one unsaturated, linear or cyclic alkyl group, $X^1$ and $L^1$ are bonded in a manner to form an allyl fragment of a linear or cyclic alkyl and permit the formation of a π type nickel-allyl bond.

4. The complex according to claim 1, in which the groups $R^1$, i.e. $R^{1a}$ and $R^{1b}$, which may be identical or different and which may or may not be bonded together, are independently selected from alkyl groups containing 1 to 15 carbon atoms and aromatic groups containing 5 to 20 carbon atoms, which may or may not be substituted and which may or may not contain heteroelements.

5. The complex according to claim 4, in which the groups $R^1$, i.e. $R^{1a}$ and $R^{1b}$, which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted, which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups, which may or may not be substituted and which may or may not contain heteroelements.

6. The complex according to claim 1, in which the group $R^2$ is selected from alkyl groups containing 1 to 15 carbon atoms and aromatic groups containing 5 to 20 carbon atoms, which may or may not be substituted and which may or may not contain heteroelements.

7. The complex according to claim 6, in which the group $R^2$ is selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-ditert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain heteroelements.

8. A process for the preparation of a complex according to claim 1, comprising bringing at least one ligand comprising said ligand fragment constituted by the atoms P, N, S and O into contact with at least one nickel precursor with an oxidation number (0), a precursor of the group $X^1$, a precursor of the group $L^1$ and optionally a precursor of the Lewis base group $L^2$.

9. The process according to claim 8, in which the nickel precursor is selected from nickel(0) bis(cycloocta-1,5-diene), nickel(0) bis(cycloocta-1,3-diene), nickel(0) bis(cyclooctatetraene), nickel(0) bis(cycloocta-1,3,7-triene), bis(o-tolylphosphito)nickel(0) (ethylene), nickel(0) tetrakis (triphenylphosphite), nickel(0) tetrakis(triphenylphosphine) and nickel (0) bis(ethylene), used alone or as a mixture.

10. A process for the preparation of a complex according to claim 1, comprising bringing at least one ligand comprising said ligand fragment constituted by the atoms P, N, S and O into contact with at least one nickel precursor with an oxidation number (+II), in the presence of a precursor of the group $X^1$, a precursor of the group $L^{1}$' a reducing agent and optionally a precursor of the Lewis base group $L^2$.

11. The process according to claim 10, in which the nickel precursor is selected from nickel (II) chloride, nickel (dimethoxyethane) chloride(II), nickel(II) bromide, nickel (II)(dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate, for example, nickel(II) phenates, nickel(II) acetate, nickel(II) trifluoroacetate, nickel(II) triflate, nickel (II) acetylacetonate, nickel(II) hexafluoroacetylacetonate, allylnickel(II) chloride, allylnickel(II) bromide, methallylnickel(II) chloride dimer, allylnickel(II) hexafluorophosphate, methallylnickel(II) hexafluorophosphate, biscyclopentadienyl nickel(II), bisallyl nickel(II) and bismethallyl nickel(II); in their hydrated or non-hydrated form, alone or as a mixture.

12. A process for the oligomerization of a feed of olefins, comprising bringing said feed into contact with a complex according to claim 1 in the presence or absence of solvent.

13. The process according to claim 12, in which the complex is used as a mixture with a compound selected from the group consisting of: tris(hydrocarbyl)aluminium compounds, chlorine-containing or bromine-containing compounds of hydrocarbylaluminium, aluminoxanes, organoboron compounds and organic compounds which are susceptible of donating or accepting a proton, used alone or as a mixture.

14. The process according to claim 12, in which the feed comprises olefins containing 2 to 10 carbon atoms.

15. The process according to claim 12, in which the reaction is an ethylene oligomerization reaction.

16. The complex according to claim 1, in which the groups $R'^1$, i.e. $R'^{1a}$, $R'^{1b}$ and $R'^{1c}$, which may be identical or different and which may or may not be bonded together, are independently selected from alkyl groups containing 1 to 15 carbon atoms and aromatic groups containing 5 to 20 carbon atoms, which may or may not be substituted and which may or may not contain hetero elements.

17. The complex according to claim 16, in which the groups $R'^1$, i.e. $R'^{1a}$, $R'^{1b}$ and $R'^{1c}$, which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted, which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di (trifluoromethyl)phenyl, benzyl, naphthyl, bisnaphthyl, pyridyl, bisphenyl, furanyl and thiophenyl groups, which may or may not be substituted and which may or may not contain heteroelements.

18. The complex according to claim 2, in which the group $R'^2$ is selected from alkyl groups containing 1 to 15 carbon atoms and aromatic groups containing 5 to 20 carbon atoms, which may or may not be substituted and which may or may not contain heteroelements.

19. The complex according to claim 18, in which the group $R'^2$ is selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-ditert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain heteroelements.

20. The complex according to claim 1, which is selected from the following complexes, C1 to C10:

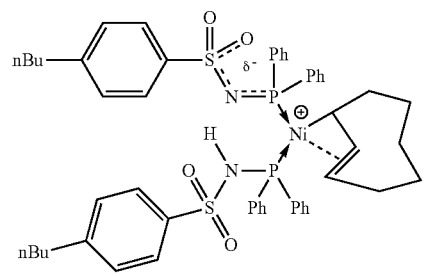

C1

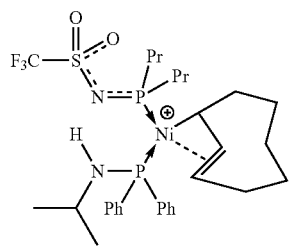

C2

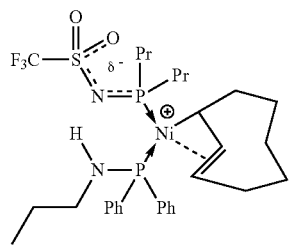

C3

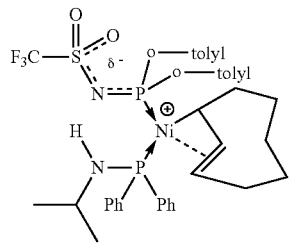

C4

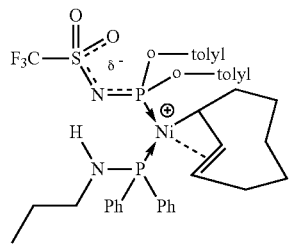

C5

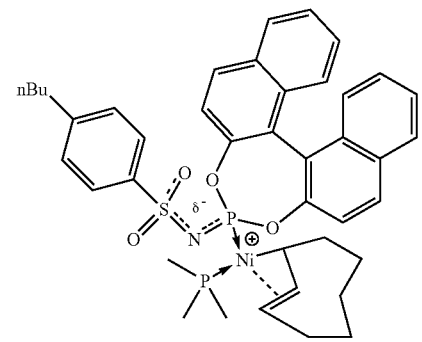

C6

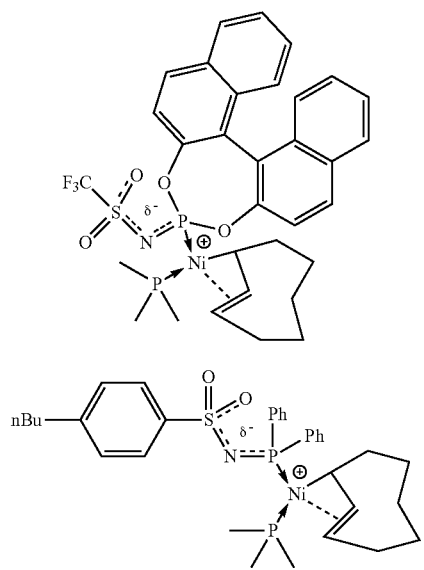
C7
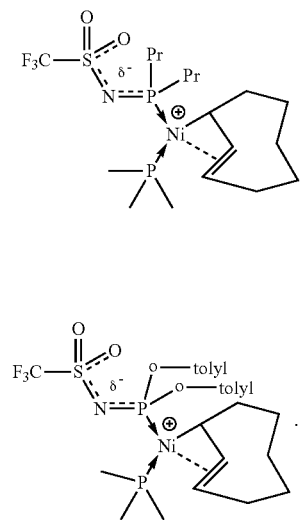
C9
C8
C10
\* \* \* \* \*